(12) United States Patent
Vissiere et al.

(10) Patent No.: US 12,042,269 B2
(45) Date of Patent: Jul. 23, 2024

(54) METHOD FOR ANALYZING THE STRIDE OF A WALKING PEDESTRIAN

(71) Applicant: SYSNAV, Vernon (FR)

(72) Inventors: David Vissiere, Vernon (FR); Marc Grelet, Vernon (FR)

(73) Assignee: SYSNAV, Vernon (FR)

( * ) Notice: Subject to any disclaimer, the term of this patent is extended or adjusted under 35 U.S.C. 154(b) by 737 days.

(21) Appl. No.: 17/253,567

(22) PCT Filed: Jun. 21, 2019

(86) PCT No.: PCT/EP2019/066534
§ 371 (c)(1),
(2) Date: Dec. 17, 2020

(87) PCT Pub. No.: WO2019/243609
PCT Pub. Date: Dec. 26, 2019

(65) Prior Publication Data
US 2021/0169374 A1 Jun. 10, 2021

(30) Foreign Application Priority Data
Jun. 21, 2018 (FR) ...................................... 1855524

(51) Int. Cl.
*A61B 5/11* (2006.01)
*A61B 5/00* (2006.01)
(Continued)

(52) U.S. Cl.
CPC ............ *A61B 5/112* (2013.01); *A61B 5/1126* (2013.01); *A61B 5/6829* (2013.01);
(Continued)

(58) Field of Classification Search
CPC ..... A61B 5/112; A61B 5/1126; A61B 5/6829; A61B 5/7278; A61B 2562/0219; G01C 19/00; G01P 13/00; G01P 15/08
See application file for complete search history.

(56) References Cited

U.S. PATENT DOCUMENTS 7,647,196 B2 * 1/2010 Kahn ................. A63B 69/0028
702/149
9,307,932 B2 * 4/2016 Mariani ................. A61B 5/112
(Continued)

FOREIGN PATENT DOCUMENTS

CN 105210067 * 12/2015
FR 3042266 A1 4/2017
(Continued)

OTHER PUBLICATIONS

International Preliminary Report on Patentability received for PCT Patent Application No. PCT/EP2019/066534, mailed on Dec. 30, 2020, 15 pages (8 pages of English Translation and 7 pages of Original Document).
(Continued)

*Primary Examiner* — Octavia Davis Hollington
(74) *Attorney, Agent, or Firm* — WOMBLE BOND DICKINSON (US) LLP (57) ABSTRACT

A method for analyzing the stride of a walking pedestrian. It includes steps of: (a) acquiring, during a recording period, measurements of a motion of a lower limb of the pedestrian, (b) determining each stride made by the pedestrian, (c) dividing the recording period into recording sub-periods, (d) estimating a characteristic quantity of the stride for several detected strides, (e) selecting at least one characteristic stride quantity in a predetermined range of percentiles within a set formed by the estimated characteristic stride quantities, ordered by increasing values and occurring during a recording sub-period, (f) repeating step (e) for several recording
(Continued)

sub-periods. The invention also concerns an equipment for analyzing the stride of a walking pedestrian, and a computer program product.

20 Claims, 3 Drawing Sheets

(51) Int. Cl.
    *G01C 19/00*     (2013.01)
    *G01P 13/00*     (2006.01)
    *G01P 15/08*     (2006.01)

(52) U.S. Cl.
    CPC ............ *A61B 5/7278* (2013.01); *G01C 19/00* (2013.01); *G01P 13/00* (2013.01); *G01P 15/08* (2013.01); *A61B 2562/0219* (2013.01)

(56) References Cited

U.S. PATENT DOCUMENTS

| | | | |
|---|---|---|---|
| 10,996,059 B2* | 5/2021 | Vissiere | ............ G01C 21/1654 |
| 11,099,029 B2* | 8/2021 | Vissiere | ............... G01C 22/006 |
| 2010/0280792 A1* | 11/2010 | Paiva Velhote Correia | ................ A61B 5/1038 702/160 |
| 2013/0123665 A1 | 5/2013 | Mariani et al. | |
| 2013/0178958 A1* | 7/2013 | Kulach | ............. A63B 24/0021 700/91 |
| 2021/0389342 A1* | 12/2021 | Kelly | ................... A61B 5/6823 |

FOREIGN PATENT DOCUMENTS

| | | | | |
|---|---|---|---|---|
| JP | 2012000343 | * | 1/2012 | |
| JP | 5117123 B2 | * | 1/2013 | ........... A61B 5/1038 |
| KR | 101252634 | * | 4/2013 | |
| KR | 20150062493 | * | 6/2015 | |
| KR | 101751760 | * | 6/2017 | |
| WO | 2014/135187 A1 | | 9/2014 | |

OTHER PUBLICATIONS

International Search Report and Written Opinion received for PCT Patent Application No. PCT/EP2019/066534, mailed on Aug. 26, 2019, 18 pages (8 pages of English Translation and 10 pages of Original Document).
Preliminary Research Report received for French Application No. 1855524, mailed on Feb. 27, 2019, 3 pages (1 page of French Translation Cover Sheet and 2 pages of original document).
Seferian et al., "Longitudinal results of magneto-inertial motion analysis in Duchenne muscular dystrophy ambulant patients", Neuromuscular Disorders, vol. 26, 2016, p. 328 (2 pages).
Tarnita, Daniela, "Wearable sensors used for human gait analysis", Romanian journal of morphology and embryology= Revue roumaine de morphologie et embryologie, Romania, vol. 57, No. 2, Jan. 1, 2016, pp. 373-382.
Seferian et al., "Poster 328 WMS 2016", Institute of Myology, 2016, 1 page.

* cited by examiner

METHOD FOR ANALYZING THE STRIDE OF A WALKING PEDESTRIAN

FIELD OF THE INVENTION

The present invention concerns the field of analysis of the stride of a walking pedestrian.

TECHNOLOGICAL BACKGROUND

Figure 1:
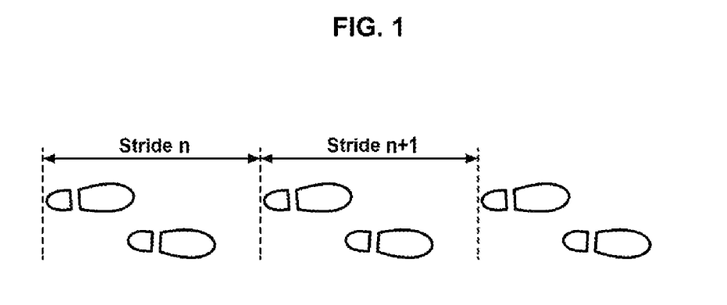
FIG. 1, already commented on, is a diagram representing strides of an individual.

A walk of an individual comprises a sequence of one or several stride(s). A stride consists of two phases: a first phase during which the foot is in contact with the ground, and a second phase during which the foot is in the air. As illustrated in FIG. 1, a stride begins when one foot touches the ground, and ends when the same foot touches the ground again.

The walk requires the use and the coordination of several muscles. The analysis of a stride can therefore be used to characterize the fitness state of an individual and in particular the muscle strength that the latter is able to develop. This muscle strength is likely to vary depending on many factors such as the fitness state, age, physical training of the individual or a treatment taken by the latter that affects his muscle efficiency.

The evolution of the characteristics of a stride over time may be representative of the evolution of the fitness state of an individual, particularly in the case of an individual with neuromuscular or neurodegenerative disease. These diseases such as Duchenne Muscular Dystrophy (DMD) result in a reduction, as the disease progresses, of the muscle capacities of the individual. This leads to an alteration of the characteristics of the strides, which typically become slower, shorter, fewer.

In a known manner, the stride of an individual can be analyzed during tests, such as the six minutes walk test (6MWT), the North Star Ambulation Assessment (test NSAA) or the timed 4-step stair climb test.

The 6MWT consists in asking the individual to walk at maximum capacity for six minutes, the distance traveled then being analyzed. The 6MWT is used in many fields, such as orthopedics or various neuro-muscular pathologies, and aims at measuring the maximum effort that the individual is able to produce, in order to characterize his fitness state in relation to a normative group. Indeed, the maximum power developed by the individual is representative of his physical state and of the power of his muscles.

The NSAA test includes 17 functional activities, including walking or running for 10 minutes, switching between sitting, standing and lying positions, climbing up and down stair steps, jumping, etc.

Finally, the timed 4-step stair climb test measures the minimum duration required for the individual to climb four stair steps.

These tests can be repeated at different times, in order to follow the evolution of the fitness state of the individual. Nevertheless, such tests are restrictive because they require to be carried out in a controlled environment (generally in a clinical center), on a particular course (indoor, flat, ideally straight course of a certain distance) and in the presence of qualified staff in order to validate the expected conditions. The individual must therefore regularly move to a clinical center to carry out the tests. In addition, the individual can carry out these tests only during one-time sessions, and the test may be biased by external conditions affecting the performance of the individual at the time of testing (temporary fatigue, motivation and concentration varying from one session to another, lane length, ground adhesion, encouragements given during the test, etc.). During the 6MWT, the individual may, voluntarily or unconsciously, walk faster or slower throughout the tests. The 4-step stair climb test can be very fast, so that biases relating to the initiation of the measurement can be observed.

Thus, the tests mentioned above may not be representative of the general fitness state of the individual, and the variability accepted for a given individual in these tests as well as the value corresponding to a clinically substantial change are very high. For example, for the 6MWT, the accepted variability is of about 15% and a clinically substantial change is on the order of 30 m.

Also in a known manner, some applications, for example pedometers, mobile phones or connected watches, allow counting the strides or the number of episodes of activity of an individual. The distance traveled by the individual can then be measured by a GPS receiver on-board such devices. However, this measurement lacks accuracy, and these applications do not determine the path of a stride. However, the number of strides is not always representative of the state of health of an individual. Indeed, this parameter is very sensitive to external variables, such as the schedule of the individual, the possible changes in his lifestyle, etc. On the other hand, an individual can make a large number of strides but at a very limited velocity or with a very short length. Finally, a weakening or a moderate improvement in the muscle power may not have an impact on the most common motions that barely approach the individual's power or endurance limit. A simple count of the number of strides, as well as the simple indication of an average stride length value, therefore do not allow characterizing in a satisfactory manner the fitness state of an individual.

In addition, document US 2013/123665 A1 proposes to analyze the path of strides of an individual using a device attached to his foot. However, this device does not perform a stride analysis representative of the maximum muscle power that an individual is able to develop, and does not allow analyzing the evolution over time of the fitness state of an individual.

SUMMARY OF THE INVENTION

One aim of the invention is to propose a method for analyzing the stride of a walking pedestrian which allows following the evolution of the fitness of the pedestrian over time.

Another aim of the invention is to deduce, from a stride analysis, information on the maximum muscle power that the individual is able to develop.

Another aim of the invention is that this method can be carried out continuously, with fewer constraints for the individual.

According to a first aspect, the invention concerns a method for analyzing the stride of a walking pedestrian, the method comprising steps of:
(a) Acquiring, during a recording period, measurements of a motion of a lower limb of the pedestrian,
(b) Determining, by a data processing unit, each stride made by the pedestrian during the recording period, based on the motion measurements,
(c) Dividing the recording period into recording sub-periods,
(d) For several detected strides, estimating a characteristic quantity of the stride, based on the motion measurements, in which the characteristic quantity is or depends on a stride length, (e) Selecting at least one characteristic stride quantity in a predetermined range of percentiles within a set formed by the estimated characteristic stride quantities, ordered by increasing values and occurring during a recording sub-period, (f) Repeating step (e) for several recording sub-periods.

Selecting, during step (e), a characteristic stride quantity in a predetermined range of percentiles for a given recording sub-period, allows having a simple and relevant indicator (in this case, a percentile of this characteristic quantity) of the fitness state of an individual during a given sub-period.

Repeating, during step (f), step (e) for several recording sub-periods, allows following the evolution of a fitness state of an individual over time.

Some preferred but non-limiting characteristics of the method are as follows, taken individually or in combination:

The characteristic quantity of a stride is an average velocity of the stride.

The predetermined range of percentiles is comprised between the $70^{th}$ and $100^{th}$ percentile. A high percentile of characteristic quantity reflects the maximum muscle power that the individual is able to develop.

The predetermined range of percentiles consists of the 95th percentile.

The acquisition of motion measurements is performed by at least one inertial sensor, such as an accelerometer or a gyrometer.

The inertial sensor is attached to the lower limb of the pedestrian, for example at an ankle of the pedestrian. Such a disposition has, in particular compared to a sensor attached to a foot of the individual, advantages in terms of ergonomics, comfort, aesthetics (sensor concealed under pants) and safety (risk of falling if a sensor attached to the foot gets caught on an external element).

The determination of a stride comprises the detection for a given moment of an acceleration of absolute value greater than a predetermined threshold, this moment defining the start of the stride and the end of a previous stride.

The length of a stride is the length of the projection of a path of the stride on a horizontal plane, or is the curvilinear length of a path of the stride, said path being estimated based on the motion measurements.

The average velocity of a stride is a ratio between the length of the stride and the duration elapsed between its start and its end.

The stride analysis method further comprises a step of verifying a criterion of belonging of a stride to a continuous sequence of several consecutive strides, steps (d) to (f) of the method being performed only on the strides belonging to a continuous sequence of several consecutive strides. Such a step allows analyzing only the strides representative of a natural and continuous walk of the individual, without the analysis being biased by trampling, isolated strides or small movements.

A stride belongs to a continuous sequence of several consecutive strides when the duration between the start of said stride and the start of a previous or next stride is comprised between 0 and 10 seconds, preferably less than 3 seconds, and when said stride is part of a sequence of at least two consecutive strides, preferably at least six consecutive strides.

A recording sub-period has a duration greater than 2 days, preferably greater than 15 days, and/or a cumulative recording duration greater than 5 hours, 10 hours or 50 hours, preferably greater than 180 hours. These criteria allow defining a sub-period including a sufficient amount of data to be representative of the daily activity of the individual, without the fitness state of the latter being likely to be significantly modified for this duration.

According to a second aspect, the invention concerns equipment for analyzing the stride of a walking pedestrian, the equipment comprising:

At least one inertial sensor to acquire, during a recording period, measurements of a motion of a lower limb of the pedestrian, A data processing unit configured to:

Determine each stride made by the pedestrian during the recording period, based on the motion measurements, Divide the recording period into sub-periods, For several detected strides, estimate a characteristic quantity of the stride, based on the motion measurements, the characteristic quantity being or depending on a stride length, Select at least one characteristic stride quantity in a predetermined range of percentiles within a set formed by the estimated characteristic stride quantities, ordered by increasing values and occurring during one of the sub-periods, Repeat the previous step for several sub-periods.

According to a third aspect, the invention concerns a computer program product comprising code instructions for the execution of a method for analyzing the stride of a walking pedestrian according to the first aspect when this program is executed by a processor.

PRESENTATION OF THE FIGURES

Other aspects, aims and advantages of the present invention will become apparent upon reading the following detailed description, given by way of non-limiting example, which will be illustrated by the following figures.

DETAILED DESCRIPTION OF ONE EMBODIMENT

Stride Analysis Equipment

Figure 2:
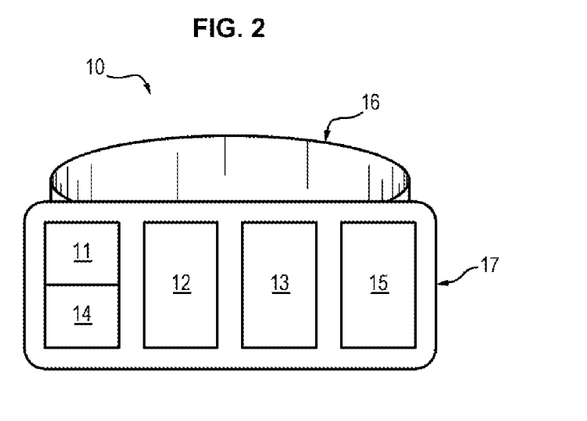
FIG. 2 is a diagram representing equipment for analyzing the stride of a walking pedestrian according to the invention.

Referring to FIG. 2, stride analysis equipment 10 comprises inertial sensors 11. The inertial sensors 11 can comprise an accelerometer and a gyrometer. Preferably, the inertial sensors 11 comprise an inertial unit comprising at least three accelerometers and three gyrometers, for example of MEMS type. The stride analysis equipment 10 can also comprise a battery, a magnetometer 14, an altimeter and/or a GPS.

The stride analysis equipment 10 can comprise a data processing unit 12 (typically a processor) for real-time implementation of the data processing. The stride analysis equipment 10 can also comprise storage means 13 (for example a flash-type memory) capable of storing the measurements made and/or data to be processed or already processed by the data processing unit 12. The stride analysis equipment 10 can also include communication means 15 for transmitting an estimated position. For example, the position of the wearer can be sent to a mobile terminal to be displayed in an interface of navigation software.

As a variant, the stride analysis equipment 10 can comprise communication means 15 for transmitting the measurements to an external device such as a mobile terminal or a remote server. These communication means 15 can implement a short-range wireless communication, for example Bluetooth or Wifi (particularly in one embodiment with a mobile terminal), or be means for connection to a mobile network (typically UMTS/LTE) for a long-distance communication. It should be noted that the communication means 15 can be for example wired connections (typically USB) for transferring the data from the local data storage means 13 to those of a mobile terminal or a server. The mobile terminal or remote server then comprises a data processing unit 12 (typically a processor) for the implementation of the data processing.

In the remainder of the present description, it will be seen that the data processing unit 12 respectively of the stride analysis equipment 10, of a mobile terminal and of a remote server can, equally and depending on the applications, perform all or part of the steps of the method.

The stride analysis equipment 10 can further comprise a casing 17 comprising the inertial sensors 11. The casing 17 can further comprise the possible data processing unit 12, storage means 13 and communication means 15.

Figure 3:
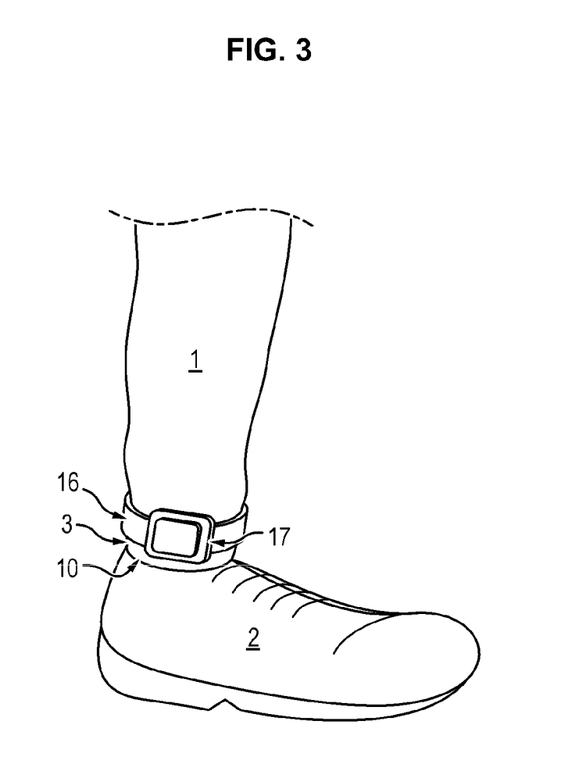
FIG. 3 is a diagram representing equipment for analyzing the stride of a walking pedestrian according to the invention, attached to a lower limb of a pedestrian.

Referring to FIG. 3, the pedestrian has at least one lower limb 1, such as a leg. It will be understood that either or each of the two lower limbs 1 of the pedestrian can be fitted with stride analysis equipment 10.

The stride analysis equipment 10 may further comprise means 16 for attachment to the lower limb 1, for example to the foot, ankle, tibia or thigh, of the pedestrian. For example, stride analysis equipment 10 comprises attachment means 16 at an ankle 3 of the pedestrian. The attachment means 16 of the casing 17 can comprise a strap around the lower limb 1 or a hook-and-loop tape which clamps the lower limb 1 and allows its secured connection to the casing 17 (therefore to the inertial sensors 11 it includes). Thus, the inertial sensors 11 have a motion in the terrestrial reference frame substantially identical to the motion of the ankle 3 of the pedestrian. Furthermore, the casing 17 and its attachment means 16 can remain concealed and protected under the pants of the individual. The latter can wear the casing 17 on a daily basis and continuously, which increases the relevance of the stride analysis. However, these inertial sensors 11 can also be disposed, for example, at the tibia or thigh of the pedestrian.

Stride Analysis Method

A method for analyzing the stride of a walking pedestrian comprises the following steps.

The inertial sensor 11 is preferably attached to the lower limb 1 of the pedestrian, for example to his foot, ankle, tibia or thigh. Preferably, the inertial sensor 11 is attached at an ankle 3 of the pedestrian.

The stride analysis method comprises a first step (a) of acquiring, during a recording period, measurements of the motion of a lower limb 1 of the pedestrian. The acquisition is preferably performed by at least one inertial sensor 11, such as an accelerometer or a gyrometer. The motion measurements are, for example, measurements of the acceleration and angular velocity of the pedestrian's ankle 3.

The recording period corresponds to the duration for which the individual is likely to wear the stride analysis equipment 10, the inertial sensors 11 then being able to make inertial measurements. For example, an individual can wear the casing 17 during the day, namely about twelve hours a day. In this case, for a 15-day recording period, the stride analysis equipment 10 will have completed 180 hours of recording. It is also possible that the individual wears the stride analysis equipment 10 twelve hours a day but only on certain days, for example every other day. In this case, for the same 15-day recording period, the stride analysis equipment 10 will only have completed 90 hours of recording.

The stride analysis method comprises a second step (b) of determining, by the data processing unit 12, each stride made by the pedestrian during the recording period, based on the motion measurements. This consists in determining that a stride has been made, as well as determining the stride start moment and the stride end moment.

In the case of stride analysis equipment attached to a shoe of the pedestrian, the determination of the stride can be made by seeking the phases of zero angular velocity and acceleration standard equal to gravity. This method is known in particular within the framework of ZUPT (Zero velocity update) methods for example [Foxlin, Eric, "Pedestrian Tracking with Shoe-Mounted Inertial Sensors", IEEE Computer Society, November/December 2005, pp. 38-46].

In the case of stride analysis equipment 10 located on the ankle 3, the measured acceleration and angular velocity are never zero, including when the foot 2 is placed on the ground, because there is a rotation around the heel during the phase where the foot 2 is in contact with the ground. Consequently, the methods such as the ZUPT method cannot be applied directly and it is preferable to rely on criteria other than zero or near-zero measurements in order to determine a stride.

According to a preferred embodiment, the determination of a stride comprises the detection, for a given moment, of an acceleration of absolute value greater than a predetermined threshold, this moment defining the start of the stride and the end of the previous stride. Indeed, at the time of impact of the foot 2 on the ground, a shock occurs on the entire lower limb 1. The absolute value of the acceleration measured by the accelerometer is then likely to exceed the predetermined threshold. This threshold may for example be comprised between 5 m/s$^2$ and 50 m/s$^2$, and be for example equal to 15 m/s$^2$.

In order to improve the accuracy of the detection of a stride, it is possible to combine the detection of an acceleration of absolute value greater than a predetermined threshold with a second stride determination criterion. This second criterion may depend on the duration elapsed since the shock, on the specific acceleration measured for a certain duration, on the acceleration peak corresponding to the shock, on the angular velocity measured for a duration elapsed since the shock, and/or on the variation of the angular velocity for a duration elapsed since the shock.

More specifically, this second criterion can be in the form of a minimization of an expression depending in particular on one or several of the parameters above. The minimum of the expression can be sought over a certain duration after the shock, for example a duration comprised between 0 seconds and 1 second after the shock, preferably a duration of 0.5 seconds after the shock. The expression to be minimized can be written in the form:

$$\Delta t_{shock} + (|accel|_{X\,ms} - \text{Shock}) + \alpha * |Vang|_{X\,ms} + \beta * \Delta Vang_X$$
$ms$, where Shock represents the value of the last detected specific acceleration peak, i.e. that has a standard greater than a predetermined threshold of 1 g, preferably greater than 1.05 g, $\Delta t_{shock}$ represents the duration elapsed between the detected shock and the current moment by the acceleration of absolute value greater than the predetermined threshold,

|accel| represents the average absolute value of the specific acceleration measured in m/s² for X ms, X being preferably comprised between 10 and 500, preferably equal to 40, α is a number, for example comprised between 1 and 100, preferably equal to 12, $|Vang|_{X\,ms}$ represents the average of the absolute value of the angular velocity measured in °/s over X ms, X being preferably comprised between 10 and 500, preferably equal to 40, β is a number, for example comprised between 1 and 100, preferably equal to 10, $\Delta Vang_{X\,ms}$ represents the variation of the angular velocity in the axis perpendicular to the leg and to the foot and measured in °/s for X ms, X being preferably comprised between 10 and 500, preferably equal to 40.

The start of a stride can correspond to the moment when the expression below is minimized, this moment also corresponding to the end of the previous stride. The combination of the detection of an acceleration of absolute value greater than a predetermined threshold and the minimization of the expression above allows determining a stride accurately and consistently.

As a variant, machine learning methods such as a neural network, a random forest, a regression or any other known statistical learning algorithm, can be used to identify a typical pattern of measurement variations, this pattern making it possible to determine a stride.

The stride analysis method comprises a third step (c) of dividing the recording period into recording sub-periods. This step allows following the evolution of the measured variables, therefore of the fitness state of an individual, sub-period after sub-period. For example, in the case where the recording period is of six months, it may be interesting to have the evolution month after month of the fitness state of the individual, the recording period then being divided into six sub-periods of a month, rather than having a single result for the entire recording period.

A recording sub-period must have a duration and a cumulative recording duration sufficiently long for the stride analysis it includes to be representative of the fitness state of an individual. According to a preferred embodiment, a recording sub-period has a duration greater than 2 days, preferably greater than 15 days, and/or a cumulative recording duration greater than 5 hours, 10 hours or 50 hours, preferably greater than 180 hours.

Indeed, if an individual did not wear the stride analysis device 10 for 15 days, the corresponding recording sub-period would have a duration of 15 days, but a cumulative recording duration of 0 hours. Such a sub-period would not comprise any stride, and therefore would not be representative of the fitness state of an individual.

A duration of 15 days and 180 hours of recording is a priori sufficiently long to guarantee a sufficient amount of data to be representative of the daily activity of the individual, while being sufficiently short for the fitness state of the individual not to be substantially modified for this duration. Such a duration also allows reducing the variability of the measurements, while not representing too great constraint for the individual wearing the stride analysis equipment 10.

As a variant, only either of these criteria of duration and cumulative recording duration of the sub-period must be met.

The stride analysis method comprises a fourth step (d) which consists, for several detected strides, in estimating a characteristic quantity of the stride, based on the motion measurements. The estimated characteristic quantity can for example be an average stride velocity or a stride length.

Figure 4:
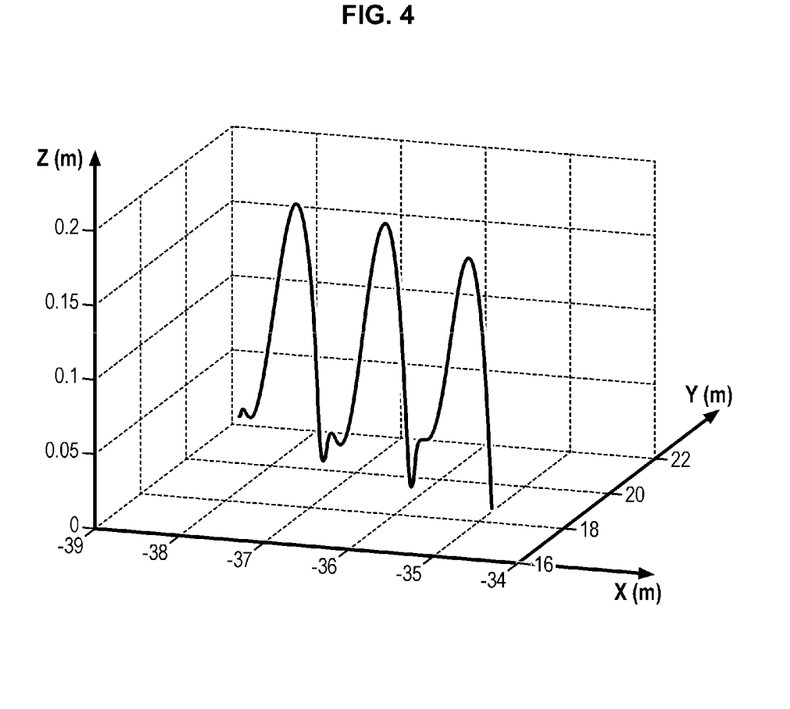
FIG. 4 is a graph representing an example of the path of an ankle during several strides.

Preferably, the data processing unit 12 makes an estimation of a path of the ankle 3 during the recording period. This estimation can be made from a double integration of the motion measurements, the double integration being preferably readjusted each time the foot 2 touches the ground. A device for making an estimation of a path of the ankle is described in document FR3 042 266. FIG. 4 represents an example of representation of a path estimated over three consecutive strides.

According to a preferred embodiment, the length of a stride is the length of the projection of the path of the stride on a horizontal plane (i.e. a plane parallel to a ground on which the individual wearing the stride analysis equipment 10 walks), the path being estimated based on the motion measurements, as described above. As a variant, the length of a stride can be, for example, the curvilinear length of the estimated path, without projecting it in the horizontal plane.

The average velocity of a stride can be defined by the ratio between the length of the stride and its duration, the duration of a stride corresponding to the duration elapsed between its start and its end.

The determination of an average stride velocity has several advantages compared to the case where the instantaneous stride velocity is considered continuously during the walk, or sampled at high frequency. Indeed, the very slow strides, which have a longer duration than the fast strides, would then be associated with a higher number of velocities compared to the faster strides, which would alter the analysis of the results. Furthermore, the derivation of the path making it possible to estimate an instantaneous velocity would generate a noise likely to affect the values of the estimated instantaneous velocities. Finally, assigning a single average velocity to a given stride allows simplifying the processing of the data by reducing the number of data to be processed, with the aim of carrying out a subsequent statistical calculation on these data.

Another embodiment consists in considering the velocity throughout each path at the sampling frequency allowed by the calculation, in a preferred embodiment between 50 Hz and 1,000 hz, preferably in the vicinity of 100 Hz.

The stride analysis method comprises a fifth step (e) of selecting at least one characteristic stride quantity (for example an average velocity and/or length) in a predetermined range of percentiles within a set formed by the estimated characteristic stride quantities, ordered by increasing values and occurring during a recording sub-period.

A stride can be associated with its date, time, and/or start and/or end moment, which allows it to be associated with a given recording sub-period. A stride can also be associated with its characteristic quantity (for example its average velocity and/or its length). The strides of a given sub-period can be ordered by increasing values of characteristic quantities.

A statistical calculation can then be carried out on a set formed by the estimated characteristic stride quantities (for example the average velocities and/or lengths), ordered by increasing values and occurring during a recording sub-period. In particular, it is possible to calculate an average and/or a percentile of this characteristic quantity, with respect to the set of the characteristic quantities of the strides of the recording sub-period. For example, it is possible to calculate the $50^{th}$ percentile, which corresponds to the median, $80^{th}$ percentile, $95^{th}$ percentile or any other percentile value of the characteristic stride quantity for a given sub-period.

A predetermined range of percentiles can be defined, this range of percentiles being relevant for the stride analysis. Particularly, the high percentiles are representative of the maximum effort and maximum muscle power that an individual is able to develop, as they reflect the fastest and/or longest strides of an individual, the walking velocity being constrained by the muscle strength state. These high percentiles are therefore particularly sensitive to the fitness state of an individual. The term "high percentile" is used in the application to refer to a percentile greater than the $70^{th}$ percentile.

Such a method for analyzing strides from a range of high percentiles is particularly suitable for walking, since an individual statistically achieves a number of longer and/or faster strides in everyday life. Particularly, the longest and/or fastest few percents of strides are representative of the maximum power that the individual is able to develop. For example, studies have shown a correlation between the effort test measurements such as the 6MWT, and the $95^{th}$ percentile of stride length and/or velocity in the same individual.

Preferably, the predetermined range of percentiles is comprised between the $70^{th}$ and the $100^{th}$ percentile. The predetermined range of percentiles may consist of the $95^{th}$ percentile.

The stride analysis method comprises a fifth step (f) of repeating step (e) for several recording sub-periods.

Such a step (f) allows accessing to the characteristic stride quantities in the predetermined range of percentiles for several recording sub-periods. Preferably, the predetermined range of percentiles is the same for each sub-period for which step (e) is repeated. Thus, it is possible to follow the evolution of the characteristic stride quantity, sub-period after sub-period. The evolution over time of the fitness state of the individual wearing the stride analysis equipment 10 can then be followed.

In a preferred embodiment, the stride analysis method further comprises a step of verifying a criterion of belonging of a stride to a continuous sequence of several consecutive strides, steps (d) to (f) of the method being performed only on the strides belonging to a continuous sequence of several consecutive strides.

Such a step allows analyzing only the data coming from a continuous and natural walk, when the individual is on his momentum. Thus, the data are not likely to be biased by a significant amount of trampling, isolated strides or micro-movements of the individual, these strides not being representative of the fitness state of the individual. Thus, the strides considered for the calculation of the predetermined range of percentiles, particularly the $95^{th}$ percentile, do not take into account the isolated strides or trampling, which eliminates the corresponding measurement bias.

Preferably, a stride belongs to a continuous sequence of several consecutive strides when the duration between the start of said stride and the start of a previous or following stride is comprised between 0 and 10 seconds, preferably less than 3 seconds, and when said stride is part of a sequence of at least two consecutive strides, preferably at least six consecutive strides.

Indeed, a duration between two strides greater than, for example, 0.5 seconds, 3 seconds or 10 seconds, indicates a probable stop of the individual between two strides. The strides then correspond to trampling, do not belong to the same walk sequence and do not reflect the fitness state of the individual.

Moreover, during a sequence of less than for example ten, six or two consecutive strides, the individual is a priori not in a normal walking pace, but in a slow pace, corresponding to trampling or to a little movement.

The combination of these two criteria allows not processing the strides that are not characteristic of a continuous walk of the individual and of the muscle power he is able to develop. As a variant, only one of the two criteria above must be verified for the steps (d) to (f) of the method to be performed.

With the same objective of only processing strides representative of the fitness state of an individual, it is possible to identify strides with an error, for example in the calculation of the path or in the determination of their start and of their end. For this purpose, the path of a stride can be compared with one or several reference path(s). The shape of the path can be studied, the existence of a maximum vertical position around the middle of the stride can be verified, ratios between height and length of the path can be defined. The strides deviating excessively from the expected characteristics in view of the reference paths are then identified as erroneous, steps (d) to (f) of the method not being performed on these strides. Thus, the data analysis is not biased by possible errors in the calculation of the path, determination of the stride, or the like.

As a variant, a machine learning algorithm such as a neural network, random forest, SVM, or any other known method, can be used to compare a stride with a reference stride database, and thus identify an erroneous stride.

In addition, it is possible to identify the first stride and the last stride of each walk, steps (d) to (f) of the method not being performed on these strides. Indeed, these strides are not either representative of a continuous walk of an individual.

It is also possible to identify the strides including a change of course, steps (d) to (f) of the method not being performed on these strides. Thus, only the strides belonging to a walk in a straight line are maintained. Indeed, a change of course leads to a slowing down, and a stride including a change of course is therefore not representative of a continuous walk and momentum of an individual. In addition, such a stride is likely to be less well determined, the pattern of rotation and acceleration of the stride being altered by the change of course.

Step (a) of the stride analysis method can be implemented by at least one inertial sensor 11 of the stride analysis equipment 10.

Steps (b) to (f) of the stride analysis method, as well as the potential additional steps described above, can be implemented by the data processing unit 12 of the stride analysis equipment 10.

The invention claimed is:

1. A method for analyzing the stride of a walking pedestrian, the method comprising steps of:
   (a) Acquiring, during a recording period, motion measurements of a motion of a lower limb of the pedestrian,
   (b) Determining, by a data processing unit, each stride made by the pedestrian during the recording period, based on the motion measurements,
   (c) Dividing the recording period into recording sub-periods, (d) For several detected strides, estimating a characteristic quantity of the stride, based on the motion measurements, in which the characteristic quantity is or depends on a stride length, (e) Calculating, with respect to a set formed by the characteristic quantities estimated for the strides of the recording sub-period, ordered by increasing values, a percentile of the characteristic quantity for that recording sub-period, the percentile being chosen in a predetermined range of percentiles, (f) Repeating step (e) for several recording sub-periods, wherein the predetermined range of percentiles is comprised between the $70^{th}$ and $100^{th}$ percentile.

2. The method according to claim 1, wherein the characteristic quantity of a stride is an average velocity of the stride.

3. The method according to claim 2, wherein the determination of a stride comprises detection for a given moment of an acceleration of absolute value greater than a predetermined threshold, this moment defining a start of the stride and an end of a previous stride, and the average velocity of a stride is a ratio between the length of the stride and a duration elapsed between its start and its end.

4. The method according to claim 1, wherein the predetermined range of percentiles consists of the $95^{th}$ percentile.

5. The method according to claim 1, wherein the acquisition of motion measurements is performed by at least one inertial sensor.

6. The method according to claim 5, wherein the at least one inertial sensor is attached to an ankle of the pedestrian.

7. The method according to claim 5, wherein the acquisition of motion measurements is performed by an accelerometer or a gyrometer.

8. The method according to claim 1, wherein the determination of a stride comprises detection for a given moment of an acceleration of absolute value greater than a predetermined threshold, this moment defining a start of the stride and an end of a previous stride.

9. The method according to claim 1, wherein the length of a stride is a length of a projection of a path of the stride on a horizontal plane, or is a curvilinear length of a path of the stride, said path being estimated based on the motion measurements.

10. The method according to claim 1, further comprising a step of verifying a criterion of belonging of a stride to a continuous sequence of several consecutive strides, steps (d) to (f) of the method being performed only on the strides belonging to a continuous sequence of several consecutive strides.

11. The method according to claim 10, wherein a stride belongs to a continuous sequence of several consecutive strides when a duration between a start of said stride and a start of a previous or next stride is comprised between 0 and 10 seconds, and when said stride is part of a sequence of at least two consecutive strides.

12. The method according to claim 11, wherein a stride belongs to a continuous sequence of several consecutive strides when the duration between the start of said stride and the start of a previous or next stride is less than 3 seconds.

13. The method according to claim 11, wherein a stride belongs to a continuous sequence of several consecutive strides when said stride is part of a sequence of at least six consecutive strides.

14. The method according to claim 1, wherein a recording sub-period has a duration greater than 2 days and/or a cumulative recording duration greater than 5 hours.

15. The method according to claim 14, wherein a recording sub-period has a duration greater than 15 days.

16. The method according to claim 14, wherein a recording sub-period has a cumulative recording duration greater than 50 hours.

17. The method according to claim 14, wherein a recording sub-period has a cumulative recording duration greater than 180 hours.

18. The method according to claim 1, comprising a further step (g) of comparing the percentile of the characteristic quantity for a first recording sub-period with the percentile of the characteristic quantity for a second recording sub-period, and deducing from that comparison an evolution over time of a fitness state of the walking pedestrian.

19. Equipment for analyzing the stride of a walking pedestrian, the equipment comprising:

At least one inertial sensor to acquire, during a recording period, measurements of a motion of a lower limb of the pedestrian, A data processing unit configured to:
  Determine each stride made by the pedestrian during the recording period, based on the motion measurements,
  Divide the recording period into sub-periods,
  For several detected strides, estimate a characteristic quantity of the stride, based on the motion measurements, the characteristic quantity being or depending on a stride length,
  Select at least one characteristic stride quantity in a predetermined range of percentiles within a set formed by the estimated characteristic stride quantities, ordered by increasing values and occurring during one of the sub-periods,
  Repeat the previous step for several sub-periods.

20. A computer program product comprising code instructions for the execution of a method for analyzing the stride of a walking pedestrian according to claim 1, when said program is executed on a computer.

* * * * *